(12) United States Patent
Han et al.

(10) Patent No.: US 10,864,300 B2
(45) Date of Patent: Dec. 15, 2020

(54) METHOD FOR PREPARING BILAYER SCAFFOLD THROUGH SINGLE PROCESS AND METHOD FOR REGENERATING TISSUE USING BILAYER SCAFFOLD OBTAINED BY PREPARING METHOD

(71) Applicant: RESEARCH COOPERATION FOUNDATION OF YEUNGNAM UNIVERSITY, Gyeongsangbuk-do (KR)

(72) Inventors: Sung Soo Han, Daegu (KR); Soon Mo Choi, Daegu (KR); Deep Ti Singh, Gyeongsangbuk-do (KR)

(73) Assignee: RESEARCH COOPERATION FOUNDATION OF YEUNGNAM UNIVERSITY, Gyeongsan-si (KR)

( * ) Notice: Subject to any disclaimer, the term of this patent is extended or adjusted under 35 U.S.C. 154(b) by 1114 days.

(21) Appl. No.: 14/905,827

(22) PCT Filed: Jul. 16, 2013

(86) PCT No.: PCT/KR2013/006355
§ 371 (c)(1),
(2) Date: Jun. 21, 2016

(87) PCT Pub. No.: WO2015/008877
PCT Pub. Date: Jan. 22, 2015

(65) Prior Publication Data
US 2016/0287754 A1    Oct. 6, 2016

(51) Int. Cl.

| | | |
|---|---|---|
| *A61L 27/36* | (2006.01) | |
| *A61L 27/56* | (2006.01) | |
| *A61F 2/30* | (2006.01) | |
| *B32B 5/32* | (2006.01) | |
| *A61L 27/38* | (2006.01) | |
| *C08J 9/30* | (2006.01) | |
| *A61L 27/60* | (2006.01) | |
| *A61F 2/10* | (2006.01) | |
| *A61F 2/28* | (2006.01) | |
| *A61L 27/26* | (2006.01) | |
| *C08J 3/24* | (2006.01) | |
| *C08J 9/00* | (2006.01) | |

(Continued)

(52) U.S. Cl.
CPC .......... *A61L 27/3687* (2013.01); *A61F 2/105* (2013.01); *A61F 2/28* (2013.01); *A61F 2/30756* (2013.01); *A61L 27/26* (2013.01); *A61L 27/3691* (2013.01); *A61L 27/3813* (2013.01); *A61L 27/3817* (2013.01); *A61L 27/3821* (2013.01); *A61L 27/56* (2013.01); *A61L 27/60* (2013.01); *B32B 5/32* (2013.01); *C08J 3/24* (2013.01); *C08J 9/0061* (2013.01); *C08J 9/28* (2013.01); *C08J 9/30* (2013.01); *C08J 9/36* (2013.01); *A61F 2002/30011* (2013.01); *A61F 2210/0004* (2013.01); *A61F 2210/0076* (2013.01); *A61F 2240/001* (2013.01); *A61L 2300/412* (2013.01); *A61L 2430/34* (2013.01); *B32B 2250/22* (2013.01); *C08J 2201/026* (2013.01); *C08J 2201/0484* (2013.01); *C08J 2207/10* (2013.01); *C08J 2301/00* (2013.01); *C08J 2305/00* (2013.01); *C08J 2323/08* (2013.01); *C08J 2325/06* (2013.01); *C08J 2329/02* (2013.01); *C08J 2329/04* (2013.01); *C08J 2333/02* (2013.01); *C08J 2339/06* (2013.01); *C08J 2367/04* (2013.01); *C08J 2371/02* (2013.01); *C08J 2375/06* (2013.01); *C08J 2379/02* (2013.01); *C08J 2389/00* (2013.01); *C08J 2489/00* (2013.01)

(58) Field of Classification Search
CPC ........ A61F 2/105; A61F 2/28; A61F 2/30756; A61L 27/00; A61L 27/3687; A61L 27/26
See application file for complete search history.

(56) References Cited

U.S. PATENT DOCUMENTS

| | | | | |
|---|---|---|---|---|
| 2007/0185585 A1* | 8/2007 | Bracy | ................. | A61L 27/3608 623/23.63 |
| 2010/0049322 A1* | 2/2010 | McKay | ............... | A61F 2/30756 623/16.11 |

(Continued)

FOREIGN PATENT DOCUMENTS

| | | |
|---|---|---|
| KR | 10-2004-0016984 A | 2/2004 |
| KR | 10-2010-0104219 A | 9/2010 |

(Continued)

OTHER PUBLICATIONS

Ma et al. "In vitro and in vivo biological performance of collagen/chitosan/silicone membrane bilayer dermal equivalent" (2007) Journal of Material Science: Material Medicine vol. 18: 2185-2191. (Year: 2007).*

(Continued)

*Primary Examiner* — Teresa E Knight
(74) *Attorney, Agent, or Firm* — Revolution IP, PLLC (57) ABSTRACT

Disclosed is a method for preparing a bilayer scaffold through single process comprising: preparing a first polymer aqueous solution; adding a second polymer into the first polymer aqueous solution and stirring a reactant; adding a surfactant into the stirred reactant and stirring the reactant at high temperature and high speed; freeze-drying the stirred reactant thereby obtaining a sponge; dipping the sponge in a cross-linking agent thereby rendering be cross-linked; and freeze-drying the cross-linked reactant.

5 Claims, 8 Drawing Sheets
Specification includes a Sequence Listing.

(51) Int. Cl.
*C08J 9/28* (2006.01)
*C08J 9/36* (2006.01)

(56) References Cited

U.S. PATENT DOCUMENTS

| | | | |
|---|---|---|---|
| 2010/0239556 A1* | 9/2010 | Rayner | A61K 38/44 424/94.4 |
| 2010/0248368 A1 | 9/2010 | Lynn et al. | |
| 2012/0015003 A1 | 1/2012 | Gleeson et al. | |
| 2012/0253456 A1 | 10/2012 | Shin et al. | |

FOREIGN PATENT DOCUMENTS

| | | |
|---|---|---|
| KR | 10-2011-0097662 A | 8/2011 |
| KR | 10-2013-0124797 A | 11/2013 |
| WO | 2008-017858 A2 | 2/2008 |
| WO | 2010-084481 A1 | 7/2010 |
| WO | 2012-134024 A1 | 10/2012 |

OTHER PUBLICATIONS

Holmberg et al. "Surfactants and Polymers in Aqueous Solution" 2002, Wiley pp. 1-37. (Year: 2002).*

Jln et al. "In-situ formation of the hydroxyapatite/chitosan-aliginate composite scaffold." (2007) Materials Letters, vol. 62: 1630-1633. (Year: 2007).*

Hago et al. "Interpenetrating Polymer Network Hydrogels Based on Gelatin and PVA by Biocompatible Approaches: Synthesis and Characterization" (May 2013), Advances in Materials Science and Engineering, vol. 2013: article ID 328763, pp. 1-8. (Year: 2013).*

Pal eta l. "Preparation and Characterization of Polyvinyl Alcohol-Gelatin Hydrogel Membranes for Biomedical Applications" (2007), AAPS PharmSciTech, vol. 8, No. 1, artcle 21, pp. E1-E5. (Year: 2007).*

International Search Report for PCT/KR2013/006355 dated Mar. 3, 2014 from Korean Intellectual Property Office.

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:

<223> OTHER INFORMATION: Forward primer for COL16A1

<400> SEQUENCE: 1
cattggtatt ggcattgcag                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for COL16A1

<400> SEQUENCE: 2
tcccaacgga gtctttcatc                                              20

<210> SEQ ID NO 3
<211> LENGTH: 20
<212> TYPE: DNA
<213> ORGANISM: Artificial Sequence
<220> FEATURE:
<223> OTHER INFORMATION: Forward primer for ITGA3

<400> SEQUENCE: 3
tattcctccg aaccagcatc                                              20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for ITGA3

<400> SEQUENCE: 4
ctcttcatct ccgccttctg                                              20

<210> SEQ ID NO 5
<211> LENGTH: 20
<212> TYPE: DNA
<213> ORGANISM: Artificial Sequence
<220> FEATURE:
<223> OTHER INFORMATION: Forward primer for VEGF

<400> SEQUENCE: 5
atctgcatgg tgatgttgga                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for VEGF

<400> SEQUENCE: 6
gggcagaatc atcacgaagt                                              20

<210> SEQ ID NO 7
<211> LENGTH: 20
<212> TYPE: DNA
<213> ORGANISM: Artificial Sequence
<220> FEATURE:
<223> OTHER INFORMATION: Forward primer for CD55

<400> SEQUENCE: 7
tccacccgtc ttgtttgtcc                                              20

```
<210> SEQ ID NO 8
<211> LENGTH: 20
<212> TYPE: DNA
<213> ORGANISM: Artificial Sequence
<220> FEATURE:
<223> OTHER INFORMATION: Reverse primer for CD55

<400> SEQUENCE: 8
ctcagagacc gacttggacc                                              20

<210> SEQ ID NO 9
<211> LENGTH: 27
<212> TYPE: DNA
<213> ORGANISM: Artificial Sequence
<220> FEATURE:
<223> OTHER INFORMATION: Forward primer for GAPDH

<400> SEQUENCE: 9
cggagtcaac ggatttggtc gtattgg                                      27

<210> SEQ ID NO 10
<211> LENGTH: 28
<212> TYPE: DNA
<213> ORGANISM: Artificial Sequence
<220> FEATURE:
<223> OTHER INFORMATION: Reverse primer for GAPDH

<400> SEQUENCE: 10
gctcctggaa gatggtgatg ggatttcc                                     28
```

METHOD FOR PREPARING BILAYER SCAFFOLD THROUGH SINGLE PROCESS AND METHOD FOR REGENERATING TISSUE USING BILAYER SCAFFOLD OBTAINED BY PREPARING METHOD

CROSS REFERENCE TO PRIOR APPLICATIONS

This application is a National Stage application of PCT International Patent Application No. PCT/KR2013/006355 filed on Jul. 16, 2013, under 35 U.S.C. § 371 which is hereby incorporated by reference in its entirety.

BACKGROUND

The present invention relates to a method for preparing bilayer scaffold through single process and a method for regenerating tissue using bilayer scaffold obtained by preparing method.

A scaffold is a physical support and adhesion substrate prepared so as to culture in vitro culture and implantation of tissue cell and is used in cell transplantation for human tissue regeneration and is very important as its use for bulk culture and proliferation of cells. It is because cell adhesion and accompanying migration and proliferation of epithelial cell occur at the contact portion between cells and a substrate.

Firstly, most of cells having biological activity go through the adhesion of the cells in order to survive in contact with internal or external materials. Especially, in survival of fibroblasts and tissue cells, cells preferentially adhere to a substrate and then a metabolism of organelle in the cytoplasm becomes active and moves to a new site so as to facilitate the proliferation and the nutrient supply.

Thus, a surface for activating deposition of a cell is the most fundamental means for proliferation of the cells. The adhesive performance of a cell substrate can be controlled artificially by components of the substrate. A scaffold is a support carrier in cell regeneration and growth, i.e. a basic material of an artificial substrate and is recently used as a container for mass culture and proliferation or flask coatings.

On the other hand, Korea Patent Publication No. 2004-0016984 discloses a carrier for culturing a cell and a tissue, and a culturing method thereof, in which the over-growth of fibroblast cells can be suppressed and target tissue or organ can be regenerated effectively. However, the above scaffold has a lot of problems that its adhesion is not enough for mass culturing of cells and its physical properties are not superior and preparation method is not simple and desired, as well.

In addition, conventionally, a bilayer scaffold was prepared by attaching each of polymer scaffolds after separately manufacturing them, however it can not fully attached and has much separation possibility and complicated process due to two-step of preparing polymer scaffolds.

Accordingly, the present inventors completed the present invention by adding an anion surfactant into solution blended with two polymers and reacting by stirring at high temperature and high speed to induce phase separation and thus identifying the production of structurally and chemically specific bilayer scaffold.

An object of the present invention is to provide a method for preparing structurally and chemically specific and unseparated bilayer scaffold through simple single process In addition, another object of the present invention is to provide a method for regenerating tissue using the bilayer scaffold.

SUMMARY

To achieve the object of the present invention, the present invention provides a method for preparing a bilayer scaffold through single process comprising: preparing a first polymer aqueous solution; adding a second polymer into the first polymer aqueous solution and stirring a reactant; adding a surfactant into the stirred reactant and stirring the reactant at high temperature and high speed; freeze-drying the stirred reactant thereby obtaining a sponge; dipping the sponge in a cross-linking agent thereby rendering be cross-linked; and freeze-drying the cross-linked reactant.

The present invention provides a method for preparing a bilayer scaffold comprising: preparing a gelatin aqueous solution by stirring gelatin in water at a temperature of 60 to 70° C. and a speed of 100 to 300 rpm so as to dissolve completely; adding polyvinylalcohol into the gelatin aqueous solution and stirring the solution; adding sodium dodecyl sulfate into the stirred solution and stirring at a temperature of 80 to 120° C. and 800 to 2000 rpm; freeze-drying the stirred solution thereby obtaining a sponge; dipping the sponge in a cross-linking agent selected from the group consisting glutaraldehyde or ethyldimethylaminopropylcarbodiimide thereby rendered be cross-linked; and freeze-drying a cross-linked reactant.

The present invention provides a method for regenerating tissue by culturing cell into the bilayer scaffold prepared by the above preparation method.

In addition, the present invention provides a composition for tissue regeneration and wound treatment comprising the above bilayer scaffold.

According to preparation method of the present invention, completely attached bilayer scaffold can be prepared through single process, differently from a conventional bilayer scaffold which is prepared by two-step process of separate manufacture of respective polymer scaffolds and then binding thereof, and the regeneration of the skin tissue which is missing due to a wound, burn, tumor, and the like can be promoted by culturing cells in the prepared bilayer scaffold and applying it to tissue generation or wound treatment of skin defect sites, or co-culturing cartilage cells and bone cells in it and applying to sites at which tissues are in contact with each other, such as bones and cartilage.

DETAILED DESCRIPTION

The present invention provides a method for preparing a bilayer scaffold through single process comprising: preparing a first polymer aqueous solution; adding a second polymer into the first polymer aqueous solution and stirring a reactant; adding a surfactant into the stirred reactant and stirring the reactant at high temperature and high speed; freeze-drying the stirred reactant thereby obtaining a sponge; dipping the sponge in a cross-linking agent thereby rendering be cross-linked; and freeze-drying the cross-linked reactant.

The first polymer and the second polymer may be different to each other and selected from the group consisting of gelatin, chitosan, elastin, hyaluronic acid, hydroxyapatite, alginate, collagen, cellulose, polyethyleneglycol (PEG), polyethylene oxide (PEO), polycaprolactone (PCL), polylactic acid (PLA), polyglycolic acid (PGA), poly[lactic-co-(glycolic acid)] (PLGA), poly[3-hydroxybutyrate]-co-(3-hydroxyvalerate) (PHBV), polydioxanone (PDO), poly[(L-lactide)-co-(carprolactone)], poly(esterurethane) (PEUU), poly[L-lactide]-co-(D-lactide)], poly[ethylene-co-(vinylalcohol)] (PVOH), polyacrylic acid (PAA), polyvinylalcohol (PVA), polyvinylpyrrolidone (PVP), polystyrene (PS), and polyaniline (PAN). Preferably, the first polymer may be gelatin and the second polymer may be polyvinylalcohol (PVA).

The surfactant may be anion surfactants and for example it may be selected from the group consisting of sodium dodecyl sulfate (SDS), ammonium lauryl sulfate (ALS), sodium lauryl ethylene sulfate (SLES), linear alkylbenzene sulfonate (LAS), α-olefin sulfonate (AOS), alkyl sulfate (AS), alkyl ether sulfate (AES) and sodium alkane sulfonate (SAS) and preferably it may be sodium dodecyl sulfate (SDS).

The stirring at high temperature and high speed is preferred to perform at a temperature of 80 to 120° C. and 800 to 2000 rpm.

The cross-linking agent may be selected from the group consisting of glutaraldehyde, ethyldimethylaminopropylcarbodiimide (EDC), genepin and transglutaminase (TG).

In addition, the present invention provides a method for preparing the above bilayer scaffold, wherein the method comprises: preparing a gelatin aqueous solution by stirring gelatin in water at a temperature of 60 to 70° C. and a speed of 100 to 300 rpm so as to dissolve completely; adding polyvinylalcohol into the gelatin aqueous solution and stirring the solution; adding sodium dodecyl sulfate into the stirred solution and stirring at a temperature of 80 to 120° C. and 800 to 2000 rpm; freeze-drying the stirred solution thereby obtaining a sponge; dipping the sponge in a cross-linking agent selected from the group consisting of glutaraldehyde or ethyldiethylaminopropylcarbodiimide thereby rendered be cross-linked; and freeze-drying a cross-linked reactant.

Furthermore, the present invention provides a method for regenerating tissue by culturing cell into the bilayer scaffold prepared by the above method.

A cell may be any one or two more selected from the group consisting of cartilage cells, bone cells, skin cells. The cell may be co-cultured by culturing different cell to each other in a top layer and a bottom layer of the bilayer scaffold.

In addition, the present invention provides a composition for tissue regeneration and wound treatment comprising the bilayer scaffold prepared by the above methods.

An embodiment of the method for preparing a bilayer scaffold according to the present invention wherein the first polymer is gelatin, the second polymer is polyvinyl alcohol (PVA), the surfactant is sodium dodecyl sulfate (SDS) and the cross-linking agent is glutaraldehyde or ethyldimethylaminopropylcarbodiimide (EDC), will be described in details.

In accordance with the an embodiment of the present invention, a bilayer scaffold can be prepared by preparing a gelatin aqueous solution by stirring gelatin in water at a temperature of 60 to 70° C. and a speed of 100 to 300 rpm so as to dissolve completely; adding polyvinylalcohol into the gelatin aqueous solution and stirring the solution; adding sodium dodecyl sulfate into the stirred solution and stirring at a temperature of 80 to 120° C. and 800 to 2000 rpm; freeze-drying the stirred reactant at −80° C. for 24 to 48 hours thereby obtaining a sponge; dipping the sponge in a cross-linking agent selected from the group consisting glutaraldehyde or ethyldimethylaminopropylcarbodiimide thereby rendered be cross-linked; and freeze-drying a cross-linked reactant at −80° C.

Firstly, gelatin aqueous solution is prepared by adding natural polymer gelatin in water and stirring at 60 to 70° C. and 100 to 300 rpm thereby dissolving completely. The gelatin aqueous solution may be 1 to 99% by weight, preferably 2.5% by weight. If gelatin content in the gelatin aqueous solution falls beyond the above range, the layer separation cannot be visualized.

If the stirring is not performed under the condition, the gelatin aqueous solution cannot be uniformly dissolved or the problem of layer separation can be occurred.

A polymer blend solution is prepared by adding polyvinylalcohol (PVA) into the gelatin aqueous solution and stirring so as to contain 1 to 99% by weight, preferably 12.5% by weight of PVA. If the PVA content is beyond the above range, the layer separation cannot be visualized.

A anionic surfactant, sodium dodecyl sulfate (SDS) is added in the stirred polymer blend solution and stirred at high temperature of 80 to 120° C. and high speed of 800 to 2000 rpm. The SDS is added so as to contain 0.01 to 2% by weight based on total polymer blend solution. If the SDS content falls beyond the above range, the reaction of layer separation cannot be controlled and it is difficult to handle it.

In addition, if the stirring at high temperature and speed is not performed under the condition, a uniform layer separation cannot be occurred and a reaction of layer separation cannot be controlled.

A sponge is obtained by freeze-drying the stirred reactant −80° C. for 24 to 48 hours and the sponge is dipped in a cross-linking agent selected from glutaraldehyde or EDC (ethyldimethylaminopropylcarbodiimide) to be cross-linked. At this time, the cross-linkage is produced by using an aqueous solution containing 0.1 to 1% by weight of the cross-linking agent such as glutaraldehyde or EDC (ethyldimethylaminopropylcarbodiimide) for 3 to 24 hours. If the content of the cross-linking agent is beyond the above range, the cross-linking reaction is not occurred thereby decomposing on the solution, or a problem in cell culture can be caused due to residues of unreacted cross-linking agent.

A bilayer scaffold is prepared by freeze-drying again the cross-linked reactant at −80° C.

Figure 1:
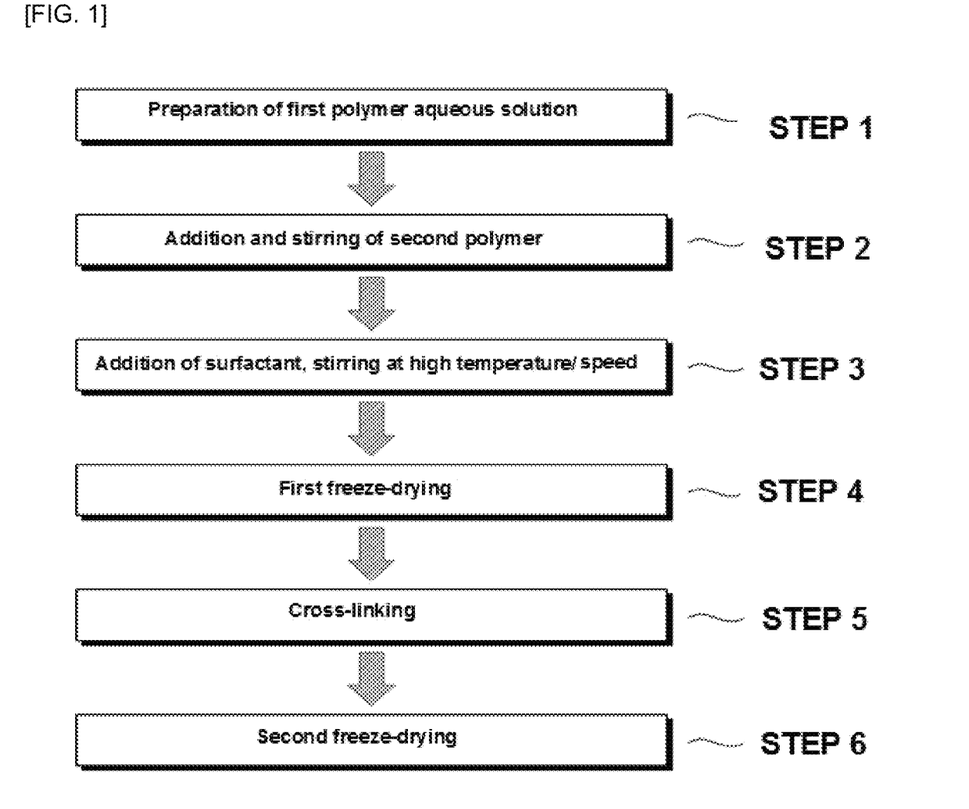
FIG. 1 illustrates a schematic flowchart of the method for preparing a bilayer scaffold according to the present invention.
Figure 2:
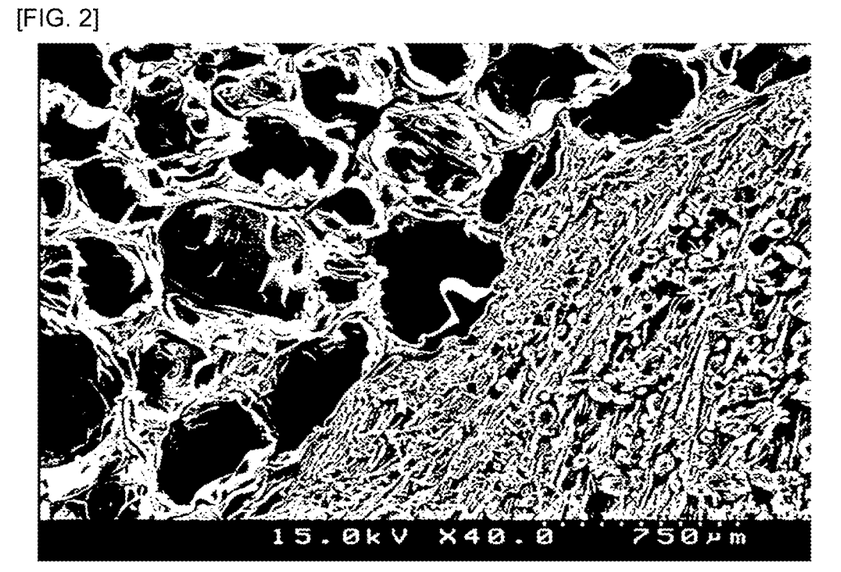
FIG. 2 is a scanning electron microscope image of a bilayer scaffold according to the invention.
Figure 3:
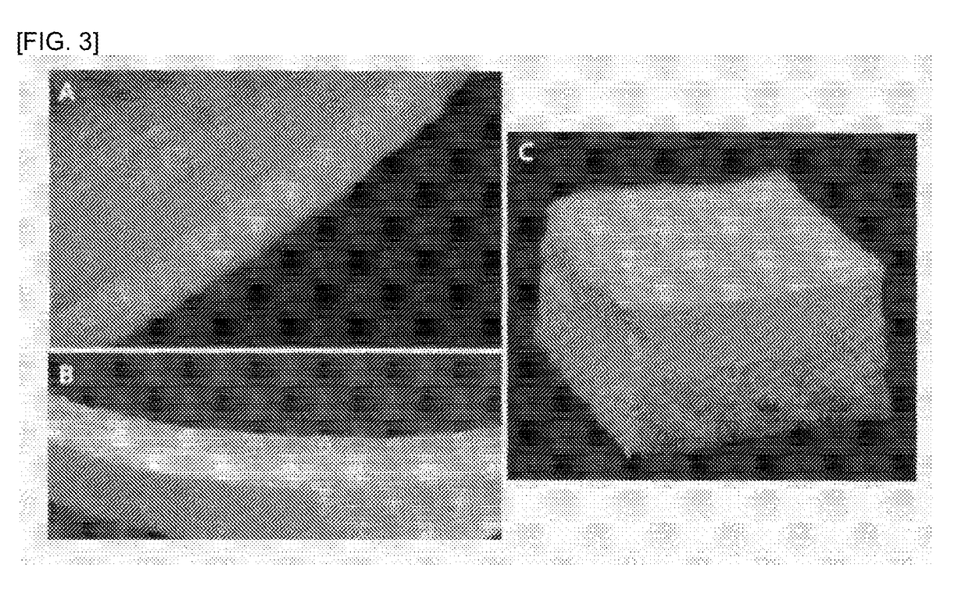
FIG. 3 is digital images of a bilayer scaffold according to the present invention (A: hydrated bilayer scaffold, B dried bilayer scaffold, C: dried bilayer scaffold before crosslinking).

According to an embodiment, bilayer scaffolds shown in FIGS. 2 and 3 of which the layer detachment is not occurred, can be prepared simply through a single process, which differs to a conventional process of bilayer scaffold in separate manufacture of respective polymer scaffolds and then binding thereof. Especially, FIG. 2 confirms a bilayer scaffold having porous gelatin layer in left side and dense PVA layer in right side.

Figure 4:
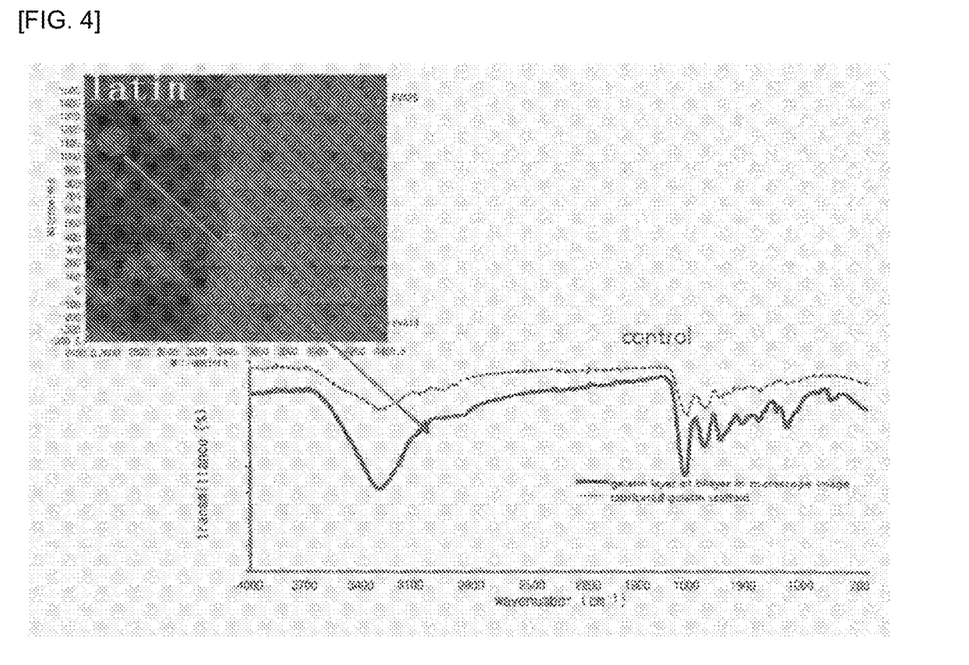
FIG. 4 is a FT-IR microscope image and a graph of a bilayer scaffold according to the invention (gelatin layer).
Figure 5:
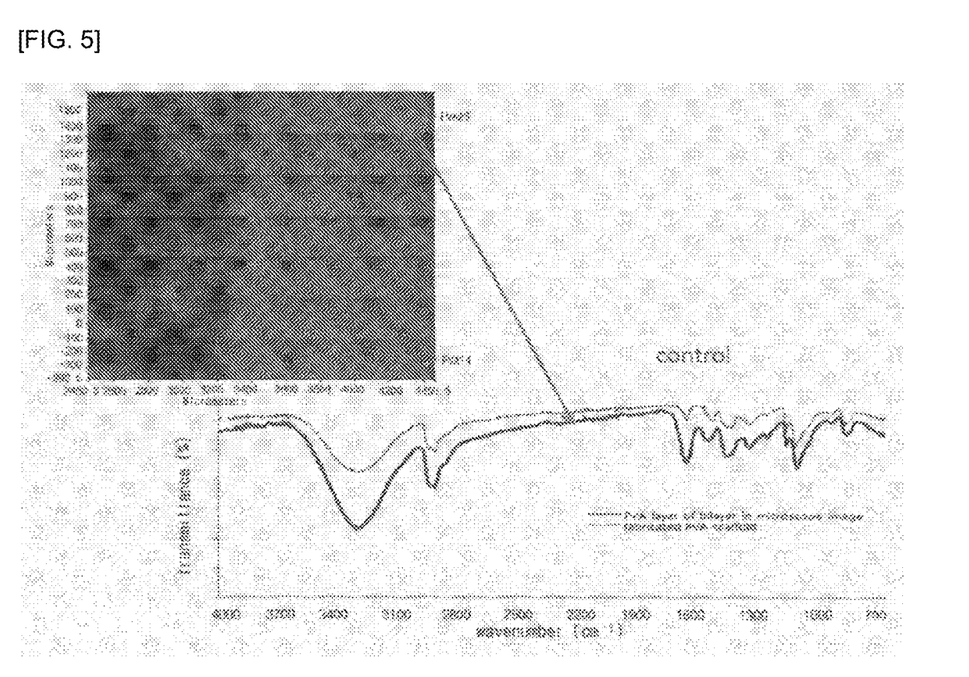
FIG. 5 is a FT-IR microscope image and a graph of a bilayer scaffold according to the invention (PVA layer).

Furthermore, FIGS. 4 and 5 represent a gelatin layer and a PVA layer in FT-IR microscope image of a bilayer scaffold according to the invention, respectively, with comparison of control of gelatin scaffold and PVA scaffold prepared separately.

Figure 6:
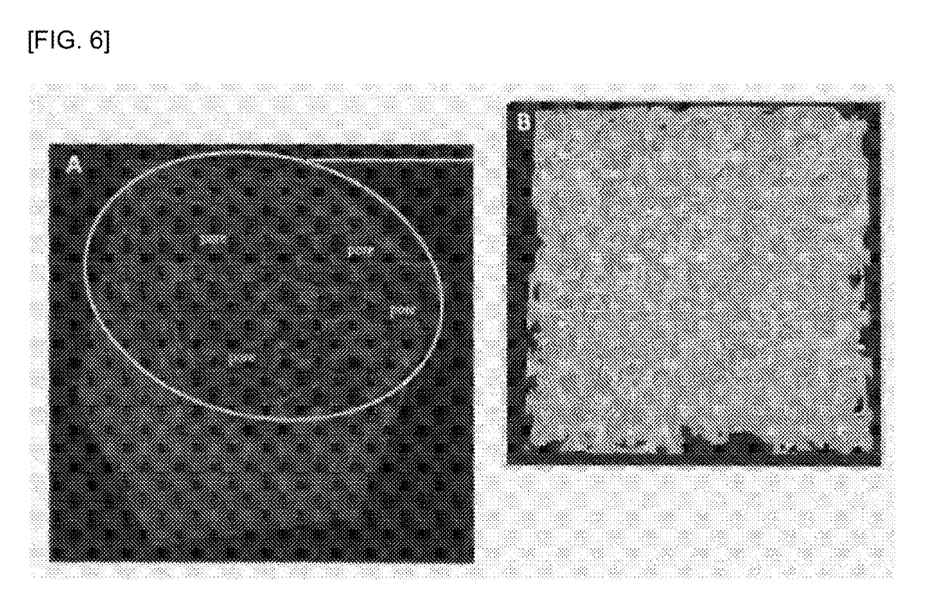
FIG. 6 is a Micro-CT image of a bilayer scaffold according to the present invention (A: bilayer scaffold, B: gelatin layer).

In addition, FIG. 6 is a Micro-CT image of a bilayer scaffold according to the present invention (A: bilayer scaffold, B: gelatin layer), in which the red part and the gray part represent a porous gelatin layer and a PVA layer having high density.

Figure 7:
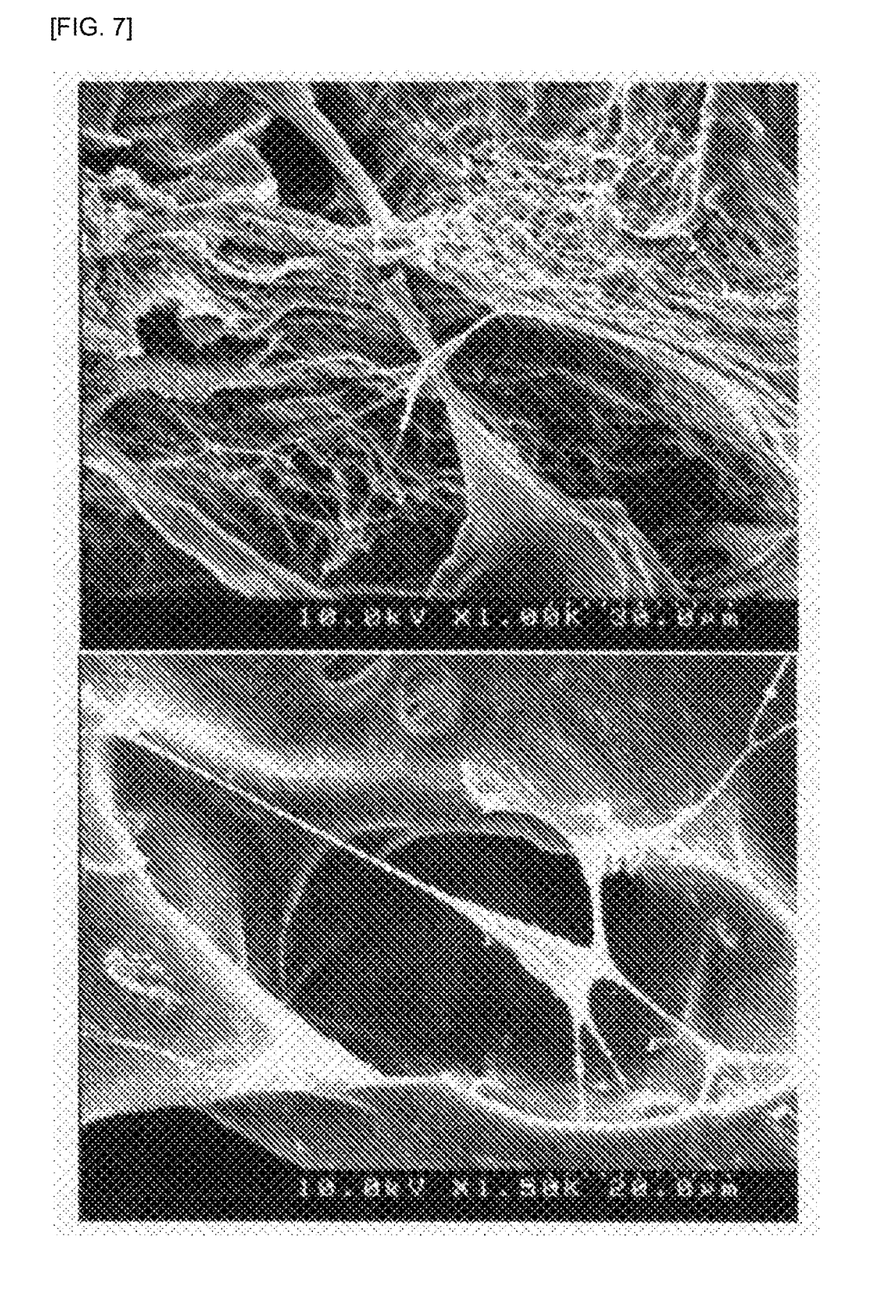
FIG. 7 is a scanning electron micrograph of a cell cultured for one day in a bilayer scaffold according to the present invention.
Figure 8:
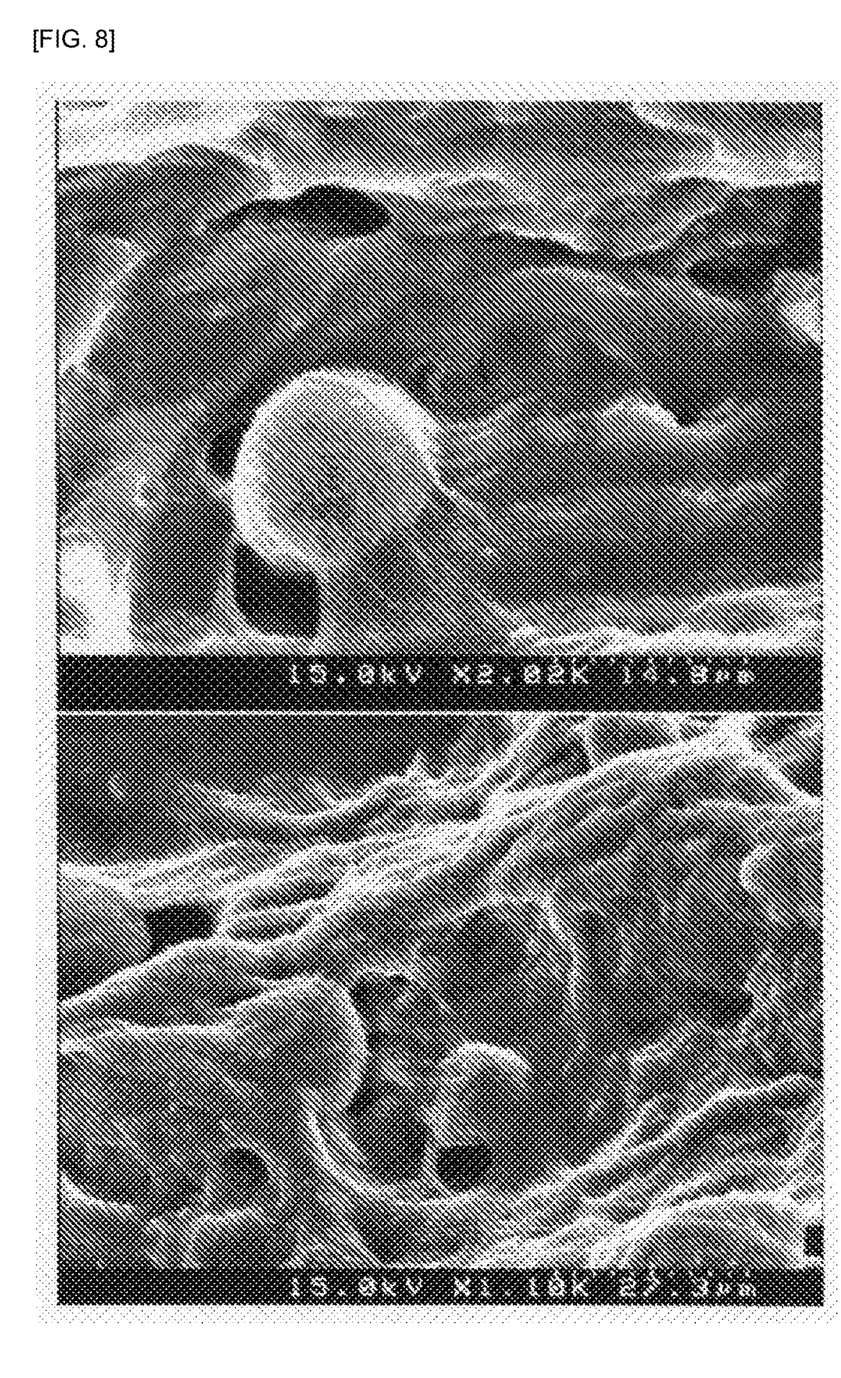
FIG. 8 is a scanning electron micrograph of a cell cultured for 5 days in a bilayer scaffold according to the present invention.

Also, as shown in FIG. 7, the culture of cells using the bilayer scaffold has resulted that it began the adherence and proliferation of cell to the scaffold in 1 day after cell seeding, and as shown in FIG. 8, it was confirmed that the cells secreted extracellular matrix (ECM) to deposit in the scaffold in 5 days after cell seeding.

Figure 9:
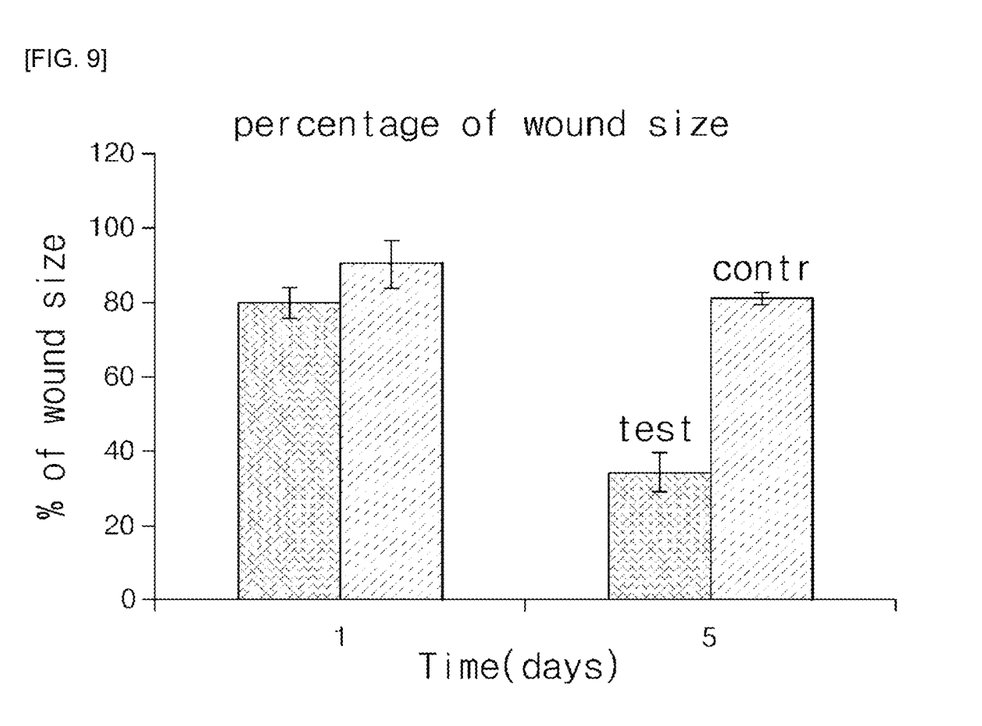
FIGS. 9 and 10 illustrate tissue regeneration effect in wound tissue by treating a bilayer scaffold according to the present invention.
Figure 10:
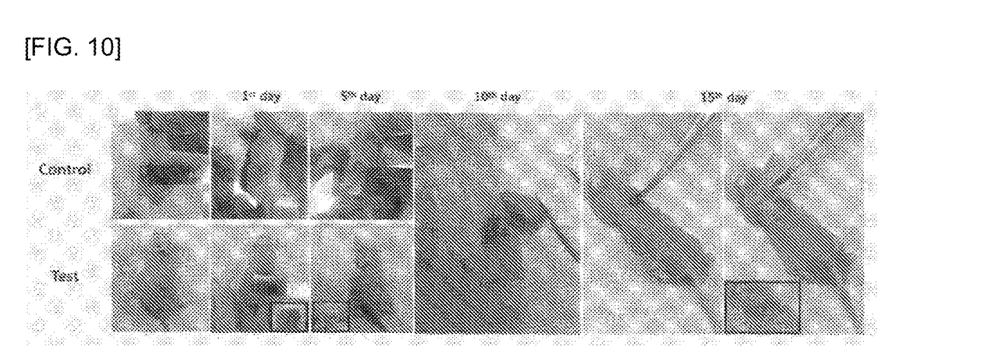

In addition, as shown in FIGS. 9 and 10 reflecting the tissue regeneration effect in the wound tissue using the bilayer scaffold, the tissue began to be bubbled from the subcutaneous skin in 1 day after the treatment of bilayer scaffold according to the present invention; the tissue was integrated in the bilayer scaffold in 5 days thereafter; in 10 days thereafter, the tissue has been regenerating and at the same time the gelatin layer began to detach by degradation spontaneously however not completely. And in 15 day thereafter, the gelatin layer of the bilayer scaffold was almost decomposed and spontaneously detached and the tissue was almost regenerated around the wound. Meanwhile, in even 5 day thereafter, the control maintained 80% of the wounded area.

Particularly, the present invention regenerates tissues without shrinkage of the wound, of which the concept is different from the tissue regeneration and cure and the wounded area becomes firm and has high density thereby being typical scar tissue thereby.

Figure 11:
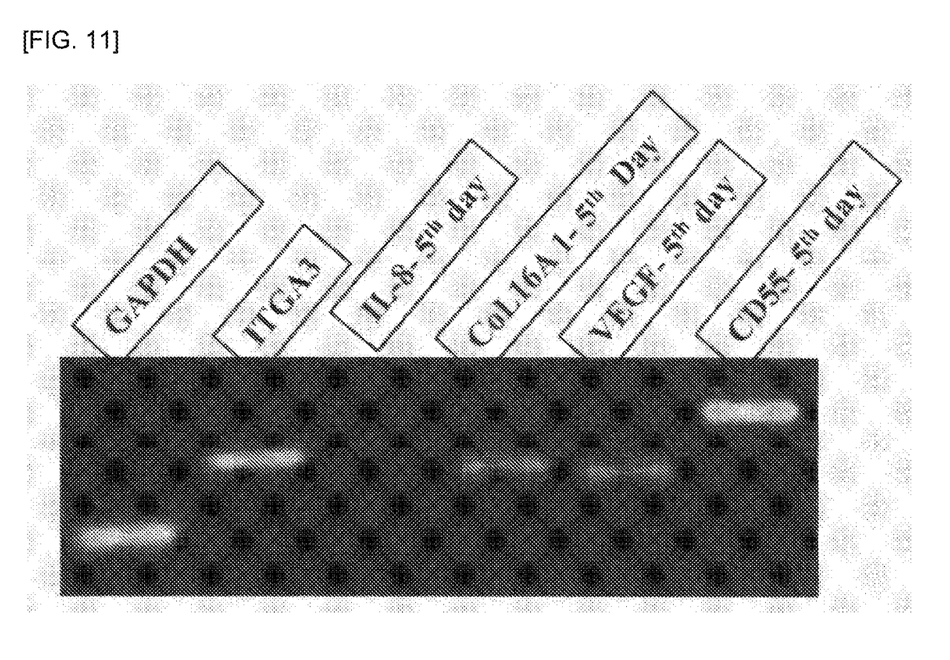
FIG. 11 is a RT-PCR analysis after treating a bilayer scaffold with wound tissue and cutting it.

In addition, FIG. 11 shows RT-PCR analysis of the tissue fragment having the bilayer scaffold in 1 day after the treatment of bilayer scaffold according to the present invention in the injury region, and in the first day ITGA 3 was expressed, which is expressed during the formation of integrin reactive with ECM (extracellular matrix) protein; in the fifth day the expression was not showed and IL-8 was not expressed to confirm that the bilayer scaffold does not cause the immune response and the expression of CD55 was increased, which inhibits the formation of inflammatory substances C5a relating to fibrils of COL16A1 forming collagen of main ingredient for ECM, vascular endothelial growth factor VEGF, and blood coagulation.

Accordingly, a bilayer scaffold according to the present invention is widely used as a material for a drug, cells, proteins and growth factors delivery or artificial skin, etc. in the tissue engineering, medicine, pharmacy and material science fields and particularly is useful for compositions for regenerating the tissue and treating the wound.

Namely, a bilayer scaffold prepared by the above preparation method is used for the tissue regeneration and the wound cure by culturing cells therein. The cell is any one or two more selected from the group consisting of cartilage cells, bone cells, skin cells, and the cell may be co-cultured by culturing different cell to each other in a top layer and a bottom layer of the bilayer scaffold.

In particular, a bilayer scaffold according to the present invention may be applied to the skin defect. In other words, cells are cultured in the bottom layer scaffold made of a natural polymer to use as a tissue regenerating layer, and the drug is loaded in the top layer scaffold made of a synthetic polymer, thereby blocking the infection of bacteria during the tissue regeneration. The natural polymer scaffold is removed by biodegradation during the tissue regeneration and the synthetic polymer scaffold is removed if the tissue regeneration is completed.

In addition, a bilayer scaffold according to the present invention may help the regeneration by co-culturing two cells and applying to sites at which tissues are in contact with each other, such as bones and cartilage. That is, a cartilage cell is cultured in the bottom layer scaffold made of a natural polymer and a bone cell is cultured in the top layer scaffold made of a synthetic polymer and the bilayer scaffold may be applied to sites at which tissues are in contact with each other for helping the tissue regeneration.

The present invention will be described more fully hereinafter with reference to the following examples which in no way should be construed as being further limiting.

<Example 1> Preparation of Bilayer Scaffold

1) Preparation of Bilayer Scaffold

A gelatin aqueous solution of 2.5% by weight was prepared and stirred at 80° C. and 300 rpm. After the gelatin was completely dissolved, polyvinyl alcohol (PVA) was added to be 10% by weight with stirring. Sodium dodecyl sulfate was added to be 0.2% by weight and stirred at high temperature of 95° C. and at high speed of 900 rpm. The stirred solution was poured into a petri dish and freeze-dried at −80° C. and for at least 24 hours to obtain a sponge. The sponge was dipped in and aqueous solution containing glutaraldehyde 0.5% by weight for at least 12 hours to cause cross-linking. Again, it was freeze-dried at −80° C. to produce a bilayer scaffold.

2) SEM and Digital Images of Bilayer Scaffold

The bilayer scaffold prepared as the above was observed by a field emission-type scanning electron microscope (FE-SEM), S-4100, HITACHI, LTD and the obtained SEM image was shown in FIG. 2, and digital images by the field emission-type scanning electron microscope (FE-SEM), S-4100, HITACHI, LTD are shown in FIG. 3. In other words, it was confirmed that the bilayer scaffold is fully adhered in the integrated form to be safe bilayer structure with no possibility of separation.

3) Analysis of FT-IR Images of Bilayer Scaffold

The bilayer scaffold prepared as the above was analyzed by scanning using a microscope FTIR Spectro photometer (Spectrum 100, PerkinElmer, USA)/imaging systems (Spotlight 200, PerkinElmer, USA) in the chamber containing liquid nitrogen and using a control of Latin scaffold or PVA scaffold which were prepared separately.

As a result, it was confirmed that there were the gelatin layer and the PVA layer of the bilayer scaffold according to the present invention, as shown in FIGS. 4 and 5.

4) Analysis of Micro-CT Images of Bilayer Scaffold

The bilayer scaffold prepared as the above was analyzed by Micro-CT images of SKYSCAN1172 (Skyscan, German), where mono chromatic beam was 40 kV, the distance between sample and detector was 45.14 mm, exposure time was 147 ms, the pixel size was fixed to 4.84362 µm.

As a result, FIG. 6 showed a Micro-CT image of a bilayer scaffold according to the present invention (A: bilayer scaffold, B: gelatin layer), in which the red part and the gray part represent a porous gelatin layer and a PVA layer having high density.

<Experimental Example 1> In Vitro Performance of Bilayer Scaffold

After preparing the bilayer scaffold prepared in Example of a diameter of 1 cm, $2 \times 10^4$ of CRL-2310 (ATCC Number; keratinocyte, human papillomavirus 16 (HPV-16) E6/E7 transformed) were divided on the bilayer scaffold. After division of cells, the SEM of FIG. 7 showed that in 1 day after the cell division, the cell began the binding to the scaffold and the regeneration thereof and FIG. 8 showed that in 5 day after the cell division, the cells secreted extracellular matrix (ECM) to confirm the deposition of ECM in the scaffold.

<Experimental Example 2> In Vivo Effect of Wound Regeneration of Bilayer Scaffold A wound of 7 mm was created using a biopsy punch and a bilayer scaffold having same size as the wound (7 mm) was bended up for gelatin layer in contact with the wound site. At this time, the scaffold was immersed in ethanol of 20, 40, 60, 80 and 100% for 1 hour, respectively for sterilization and finally in ethanol of 70% for 24 hours and in PBS buffer at room temperature for 3 hours to use in the experiments. The control group was kept with leaving the wound, while the created wound of the test group was covered with the scaffold according to the present invention.

As a result, as shown a photograph in 1 day after the treatment of the bilayer scaffold in FIGS. 9 and 10, the tissue began to be bubbled from the subcutaneous skin, while at least 90% of the wound remained in the control, and the size of the wound in the test group was decreased to 80%. From the photograph in 5 days thereafter, the tissue was integrated in the bilayer scaffold according to the present invention, the wound in the control group was decreased to 80% while the size of the wound in the test group was decreased 40% and less of the original size. From the photograph in 10 days thereafter, the tissue has been regenerating and even the regeneration of the tissue was not completed, the tissue was be bubbled enough to fully cover the wound and at the same time the gelatin layer was decomposed to detach the scaffold spontaneously however not completely. And from the photograph in 15 day thereafter, the gelatin layer of the bilayer scaffold was almost decomposed and spontaneously detached by itself and the tissue was almost regenerated around the wound.

<Experimental Example 3> Analysis by RT-PCR

The wound was treated with a bilayer scaffold according to the present invention and in 1 day thereafter the tissue around the bilayer scaffold was cut to perform RT-PCT analysis in the same manner as Experimental example 2. The condition of RT-PCR was as follows: at 94° C. for 30 seconds (denaturation), at 55-60° C. for 30 seconds according to the melting point of the primer (annealing), and 72° C. for 1 minute (extension), for 30 cycles, and finally at 72° C. for 10 minutes (final extension). The thus obtained PCR product was analyzed by gel electrophoresis. At this time, the primer set used is as follows.

TABLE 1

| Amplication subject | Forward direction primer | Reverse direction primer |
|---|---|---|
| COL16A1 | cattggtattggcat tgcag (SEQ ID No. 1) | tcccaacggagtctt tcatc (SEQ ID No. 2) |
| ITGA3 | tattcctccgaacca gcatc (SEQ ID No. 3) | ctcttcatctccgcc ttctg (SEQ ID No. 4) |
| VEGF | ATCTGCATGGTGATG TTGGA (SEQ ID No. 5) | GGGCAGAATCATCAC GAAGT (SEQ ID No. 6) |
| CD55 | TCCACCCGTCTTGTT TGTCC (SEQ ID No. 7) | CTCAGAGACCGACTT GGACC (SEQ ID No. 8) |
| GAPDH | CGGAGTCAACGGATT TGGTCGTATTGG (SEQ ID No. 9) | GCTCCTGGAAGATGG TGATGGGATTTCC (SEQ ID No. 10) |

As a result of FIG. 11, in the first day ITGA 3 was expressed, which is expressed during the formation of integrin reactive with ECM (extracellular matrix) protein; in the fifth day the expression was not showed and IL-8 was not expressed to confirm that the bilayer scaffold does not cause the immune response. The expression of CD55 was increased, which inhibits the formation of inflammatory substances C5a relating to fibrils of COL16A1 forming collagen of main ingredient for ECM, vascular endothelial growth factor VEGF, and blood coagulation.

Although the present invention has been described in detail with reference to the specific features, it will be apparent to those skilled in the art that this description is only for a preferred embodiment and does not limit the scope of the present invention. Thus, the skilled in the art can make various modifications and changes within the substantial scope of the present invention defined by the appended claims and equivalents thereof.

The invention claimed is:

1. A method for preparing a bilayer scaffold through single process, comprising:
   preparing a gelatin aqueous solution by stirring gelatin in water at a temperature of 60 to 70° C. so as to dissolve completely;
   preparing a polymer blend solution by adding polyvinyl alcohol into the gelatin aqueous solution and stirring to create a polymer blend solution;
   adding sodium dodecyl sulfate into the polymer blend solution and stirring at a temperature of 80 to 120° C.;
   freeze-drying the stirred solution thereby obtaining a sponge;
   dipping the sponge in a cross-linking agent selected from the group consisting of glutaraldehyde or ethyldiethylaminopropylcarbodimide thereby rendering the sponge cross-linked; and
   freeze-drying the cross-linked sponge,
   wherein the gelatin aqueous solution includes 2.5% by weight of gelatin,
   wherein the polymer blend solution includes 10% by weight of polyvinylalcohol.

2. A method for regenerating tissue by culturing cells into the bilayer scaffold prepared by the method according to claim 1.

3. The method for regenerating tissue according to claim 2, wherein the type of cell is any one of or two or more cell types selected from the group consisting of cartilage cells, bone cells, and skin cells.

4. The method for regenerating tissue according to claim 2, comprising culturing a first cell type in a top layer and culturing a second cell type in a bottom layer of the bilayer scaffold.

5. A composition for tissue regeneration and wound treatment comprising a bilayer scaffold prepared by the method of claim 1.

* * * * *